(12) United States Patent
Hansen (10) Patent No.: US 9,829,386 B2
(45) Date of Patent: Nov. 28, 2017

(54) APPARATUS AND METHOD FOR DETERMINING DENATURATION THERMOGRAMS OF BLOOD PLASMA OR SERUM

(71) Applicant: Brigham Young University, Provo, UT (US)

(72) Inventor: Lee D. Hansen, Saratoga Springs, UT (US)

(73) Assignee: Brigham Young University, Provo, UT (US)

( * ) Notice: Subject to any disclaimer, the term of this patent is extended or adjusted under 35 U.S.C. 154(b) by 734 days.

(21) Appl. No.: 14/282,923

(22) Filed: May 20, 2014

(65) Prior Publication Data

US 2014/0362888 A1    Dec. 11, 2014

Related U.S. Application Data

(60) Provisional application No. 61/832,792, filed on Jun. 8, 2013.

(51) Int. Cl.
| | | |
|---|---|---|
| *G01K 17/00* | (2006.01) | |
| *G01N 25/00* | (2006.01) | |
| *G01K 3/00* | (2006.01) | |
| *G01K 1/00* | (2006.01) | |
| *G01K 3/14* | (2006.01) | |
| *G01N 33/49* | (2006.01) | |
| *G01N 25/48* | (2006.01) | |
| *G01K 7/36* | (2006.01) | |

(52) U.S. Cl.
CPC ............... *G01K 3/14* (2013.01); *G01K 7/36* (2013.01); *G01N 25/005* (2013.01); *G01N 25/4846* (2013.01); *G01N 33/49* (2013.01)

(58) Field of Classification Search
USPC .................................. 374/12, 33, 137, 208
See application file for complete search history.

(56) References Cited

U.S. PATENT DOCUMENTS 3,572,084 A * 3/1971 May ...................... G01N 25/72
                                                            374/10
3,841,155 A * 10/1974 Koehler ............... G01N 25/486
                                                            374/33

* cited by examiner

Primary Examiner — Mirellys Jagan
(74) Attorney, Agent, or Firm — Kunzler PC (57) ABSTRACT

An apparatus for determining thermograms of blood plasma or serum includes two or more reaction vessels that each comprise a temperature sensing coil and a heating coil that is coaxial with and exterior to, or interleaved with, the temperature sensing coil. The apparatus also includes a heat conductive body having two or more cavities formed therein for receiving the reaction vessels. A corresponding method includes activating the heating coils of the reaction vessels and collecting temperature data for the reaction vessels with the temperature sensing coils.

20 Claims, 7 Drawing Sheets

APPARATUS AND METHOD FOR DETERMINING DENATURATION THERMOGRAMS OF BLOOD PLASMA OR SERUM

CROSS-REFERENCE TO RELATED APPLICATIONS

This application claims the benefit of U.S. provisional application 61/832,792 entitled "Differential Scanning calorimeter Design for Determining Thermograms of Denaturation of Blood Plasma or Serum" and filed on 8 Jun. 2013. The foregoing application is incorporated herein by reference.

BACKGROUND

Technical Field

The subject matter disclosed herein relates generally to calorimeters and specifically to differential calorimeters for determining denaturation thermograms of blood plasma or serum.

Discussion of the Background

Denaturation thermograms of blood plasma or serum have been found to be a useful means for determining whether an individual has a specific medical condition such as cervical cancer. Currently, however, the high cost of differential scanning calorimeters that are used to generate denaturation thermograms restricts their use to high-end institutions such as cancer research facilities. The embodiments disclosed herein were developed in response to these issues.

SUMMARY OF THE INVENTION

The present invention has been developed in response to the present state of the art, and in particular, in response to the problems and needs in the art that have not yet been fully solved by currently available differential calorimeters. Accordingly, the present invention has been developed to provide a method, apparatus, and computer readable medium for determining thermograms of blood plasma or serum that overcome shortcomings in the art.

As described herein, an apparatus for determining thermograms of blood plasma or serum includes two or more reaction vessels that each comprise a temperature sensing coil and a heating coil that is coaxial with and exterior to, or interleaved with, the temperature sensing coil. The apparatus also includes a heat conductive body having two or more cavities formed therein for receiving the reaction vessels. A corresponding method includes activating the heating coils of the reaction vessels and collecting temperature data for the reaction vessels with the temperature sensing coils.

It should be noted that references throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following description and appended claims, or may be learned by the practice of the invention as set forth hereinafter.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

Figure 1A:
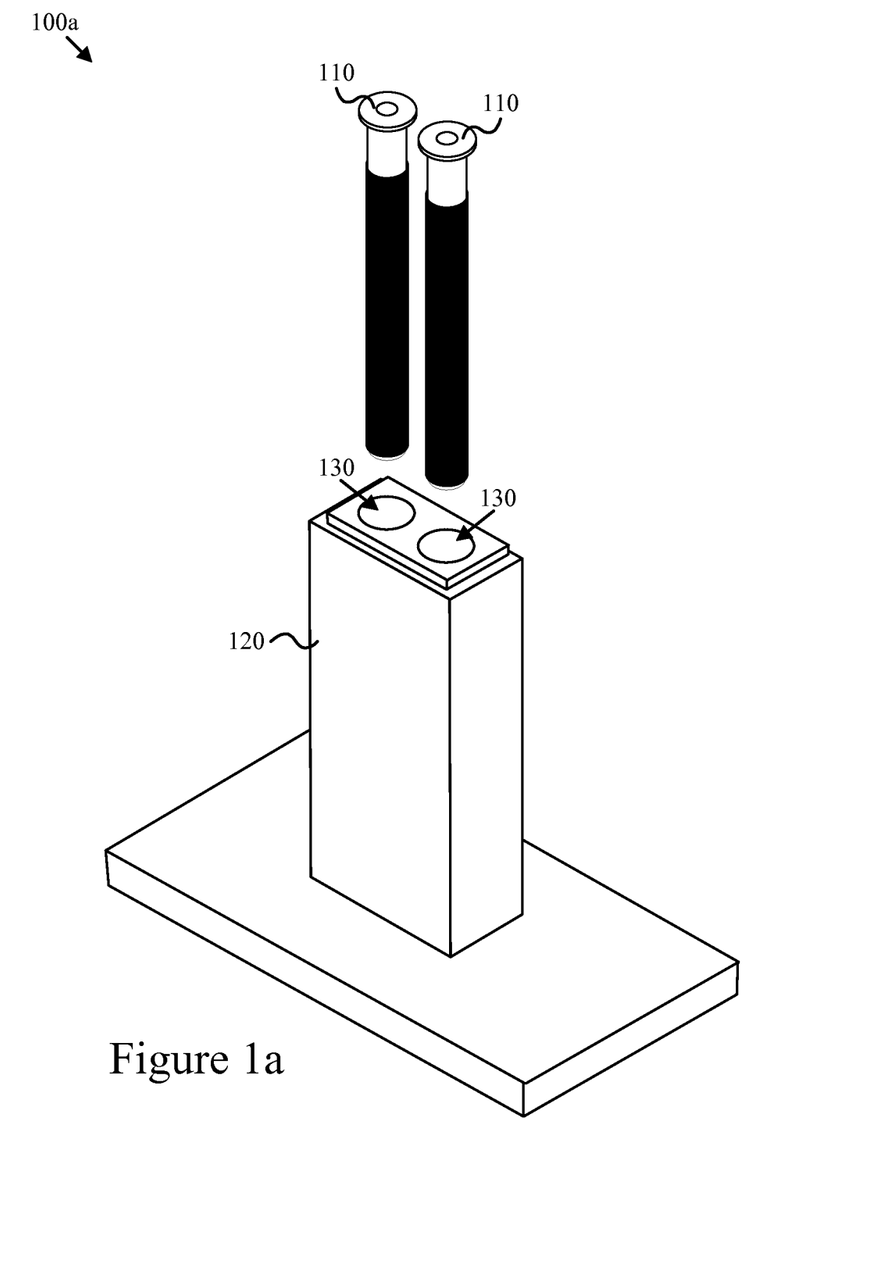
FIGS. 1a-1c are perspective view drawings of various embodiments of a thermogram collection apparatus.
Figure 1B:
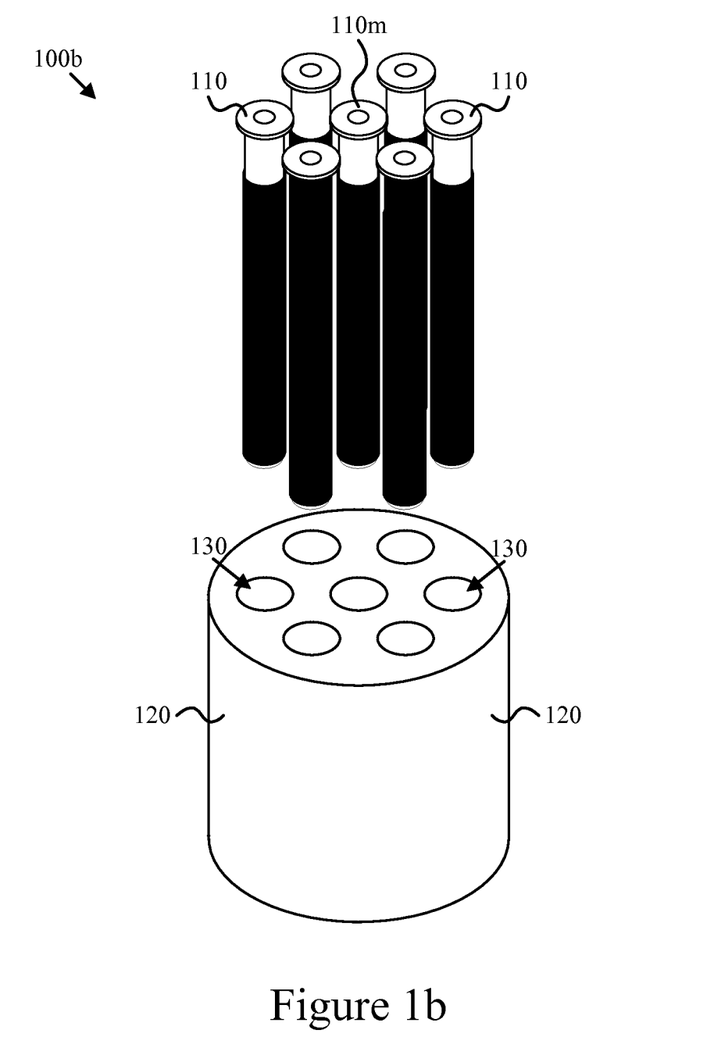
Figure 1C:
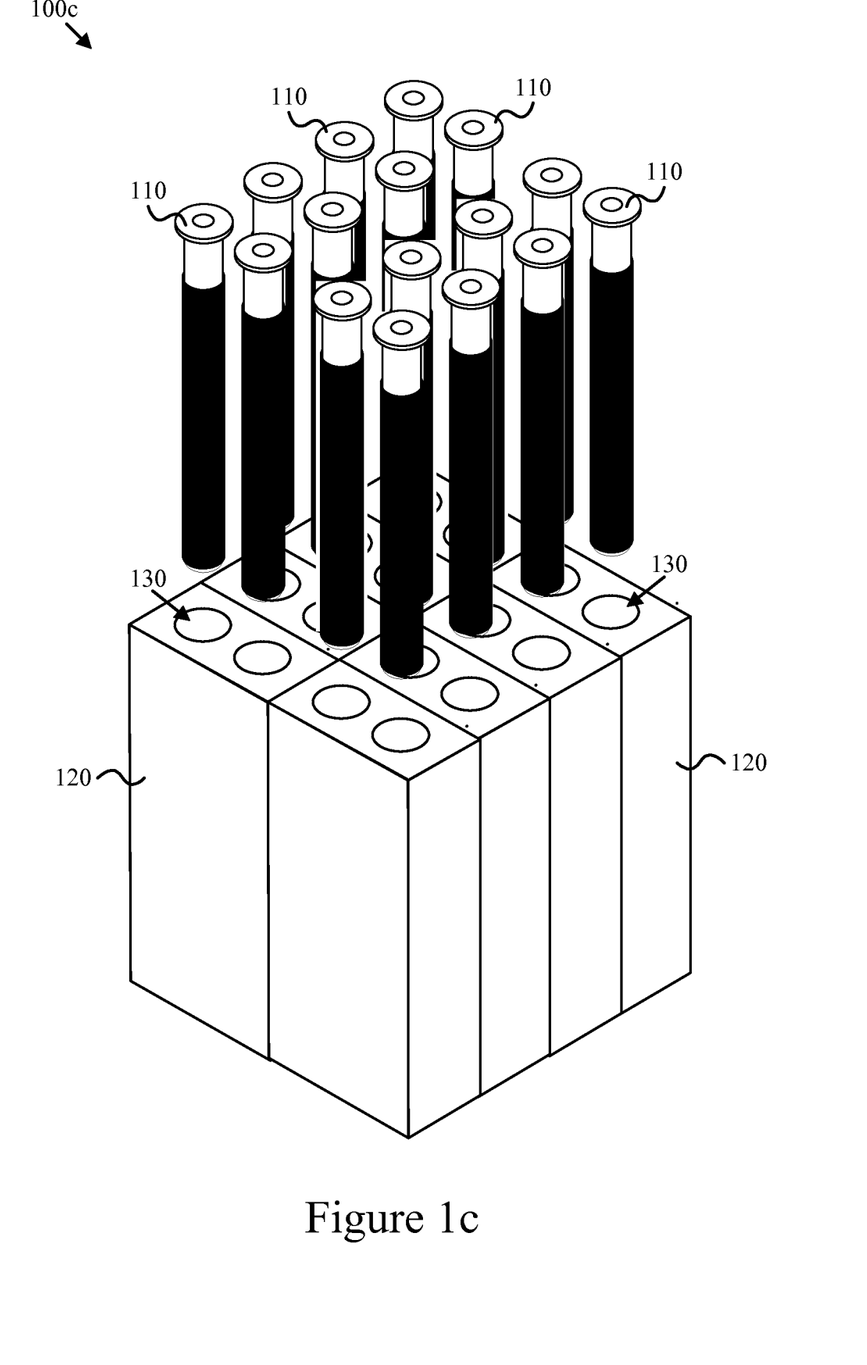

FIGS. 1a-1c are perspective view drawings of various embodiments of a thermogram collection apparatus 100. As depicted, the thermogram collection apparatus 100 includes two or more reaction vessels 110, and at least one heat conductive body 120. The heat conductive bodies 120 may have two or more cavities 130 formed therein for receiving the reaction vessels 110. The thermogram collection apparatus may also include one or more data acquisition units and processors (not shown) for controlling the apparatus 100 and collecting data therefrom. Heating leads and temperature sensing leads (not shown) may be used to connect the reaction vessels to the data acquisition units and processors. In some embodiments, electrical connectivity to the heating leads and the temperature sensing leads occurs automatically when a reaction vessel 110 is inserted into a cavity 130 of a heat conductive body 120.

FIG. 1a depicts a basic configuration 100a for thermogram collection apparatus 100 that has two reaction vessels 110, FIG. 1b depicts a circular configuration 100b with 7 reaction vessels 110, and FIG. 1c depicts a modular configuration 100c with 16 reaction vessels 110. One or more of the reaction vessels 110 in each configuration may be used as differential reference for a thermogram by filling the selected reaction vessel(s) 110 with an inert liquid such as distilled water. For example, the reaction vessel 110m shown in the middle of the circular configuration 100b of FIG. 1b may be used as a differential reference for a thermogram.

FIGS. 2a-2e are cross-sectional views depicting various embodiments of the reaction vessel 110 usable with the apparatus 100. Referring to FIGS. 2a-2e while continuing to refer to FIGS. 1a-1c, each reaction vessel 110 may include a temperature sensing coil 112, and a heating coil 114 that is coaxial with the temperature sensing coil 112. The temperature sensing coil 112 may be used to sense the temperature of the contents of the reaction vessel 110, while the heating coil 114 may be used to control (i.e., drive) a temperature profile surrounding the reaction vessel 110 and facilitate denaturation of the contents of the reaction vessel and collection of a thermogram.

The temperature sensing coil 112 may comprise a temperature sensitive material whose resistance is substantially sensitive to changes in temperature such as nickel, copper, iron, platinum and various alloys. The heating coil 114 may be exterior to, (e.g., FIGS. 2*a*-2*d*) or interleaved with, (e.g., FIG. 2*e*) the temperature sensing coil 112. The heating coil 114 may comprise an electrically resistive material such as constantan and manganin that has a resistance that is substantially constant over a wide range of temperatures resulting in a simplified relationship between driving current and coil temperature. However, one of skill in the art will appreciate that a material whose resistance varies with temperature may be used when compensated for by a current driving circuit or program (not shown).

In some embodiments, (e.g., FIGS. 2*a* and 2*b*) the reaction vessel also includes a heat conductive tube 116 that is coaxial with the temperature sensing coil 112 and the heating coil 114. The heat conductive tube may be interior to both the temperature sensing coil 112 and the heating coil 114 (e.g., FIG. 2*a*) or placed between the temperature sensing coil 112 and the heating coil 114 (e.g., FIG. 2*b*). The heat conductive tube 116 may be made of a heat conductive material such as aluminum, copper, silver or gold that facilitates both longitudinal and lateral heat flow and results in substantially constant temperatures within the reaction vessel.

Similar to the heat conductive tube 116, the heat conductive bodies 120 may be made of a heat conductive material such as aluminum, copper, silver or gold. The heat conductive bodies 120 may have substantially greater mass than the reaction vessels 110 in order to function essentially as a constant temperature source or sink while collecting calorimetric data from the reaction vessels 110.

The reaction vessels 110 may also include a sample tube 118 that is coaxial with and interior to the temperature sensing coil. The sample tube 118 may comprise glass or another unreactive material that is suitable for containing samples. The sample tube 118 may or may not have a circular cross-section. For example, the sample tube may have a square or rectangular cross-section.

Figure 2A:
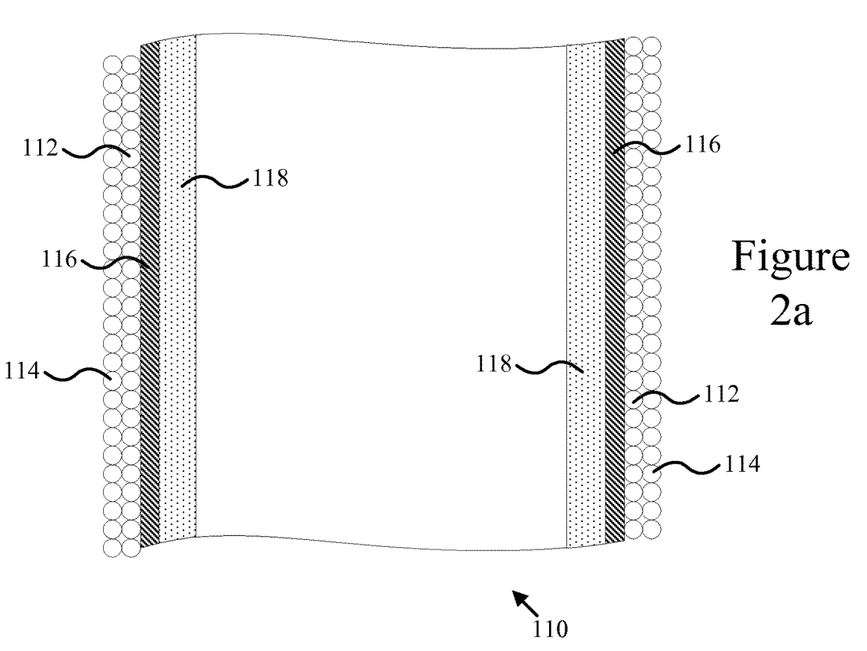
FIGS. 2a-2e are cross-sectional views depicting various embodiments of a reaction vessel suitable for collecting denaturation thermograms.
Figure 2B:
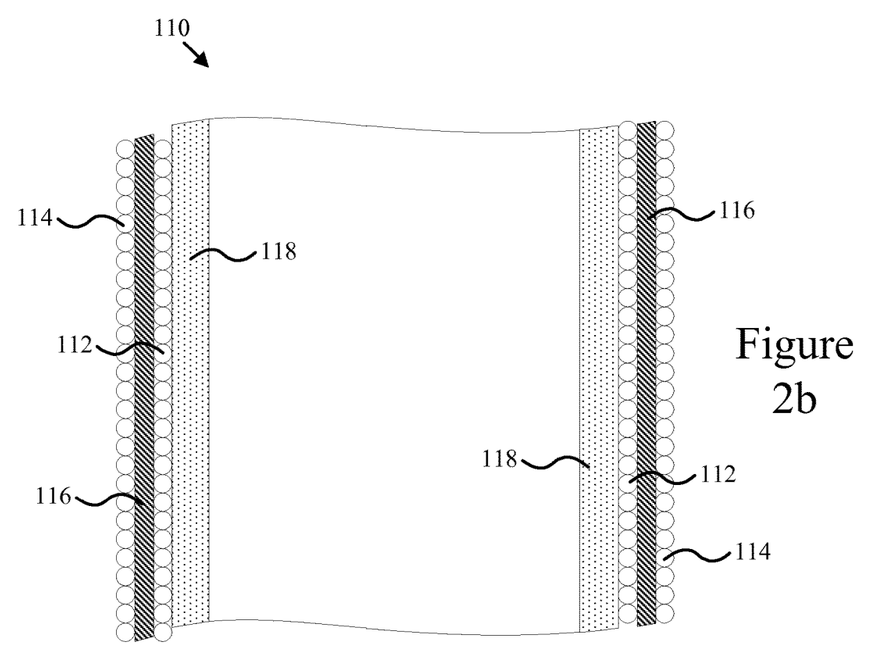
Figure 2C:
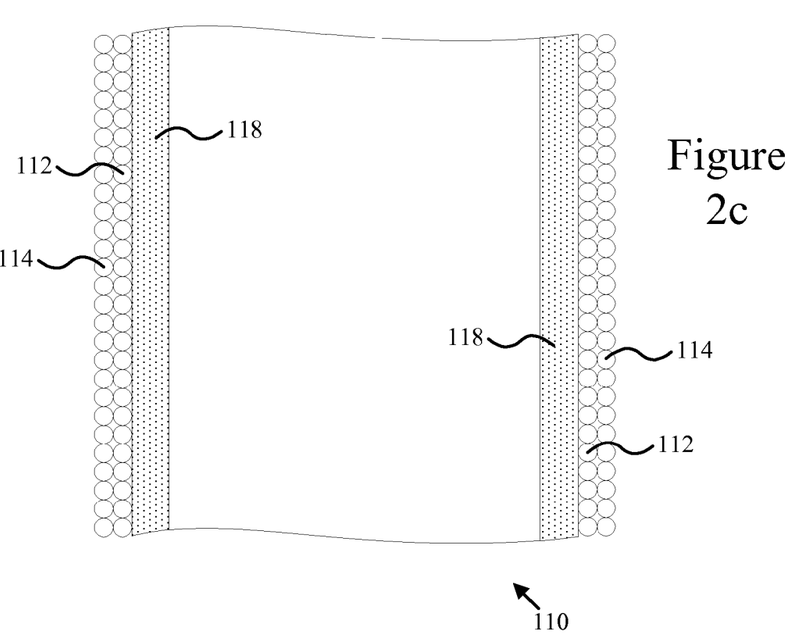
Figure 2D:
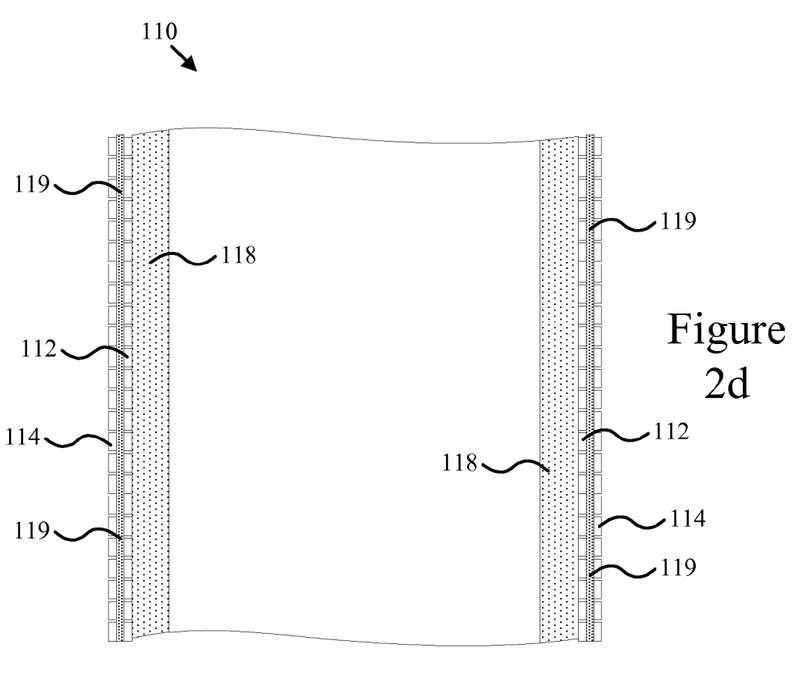

FIG. 2*d* depicts an embodiment of the reaction vessel 110 with an electrically insulating layer 119 disposed between the temperature sensing coils 112 and the heating coils 114. In some embodiments, the electrically insulating layer 119 and the coils 112 and 114 are formed via photolithography on the sample tube 118.

Figure 2E:
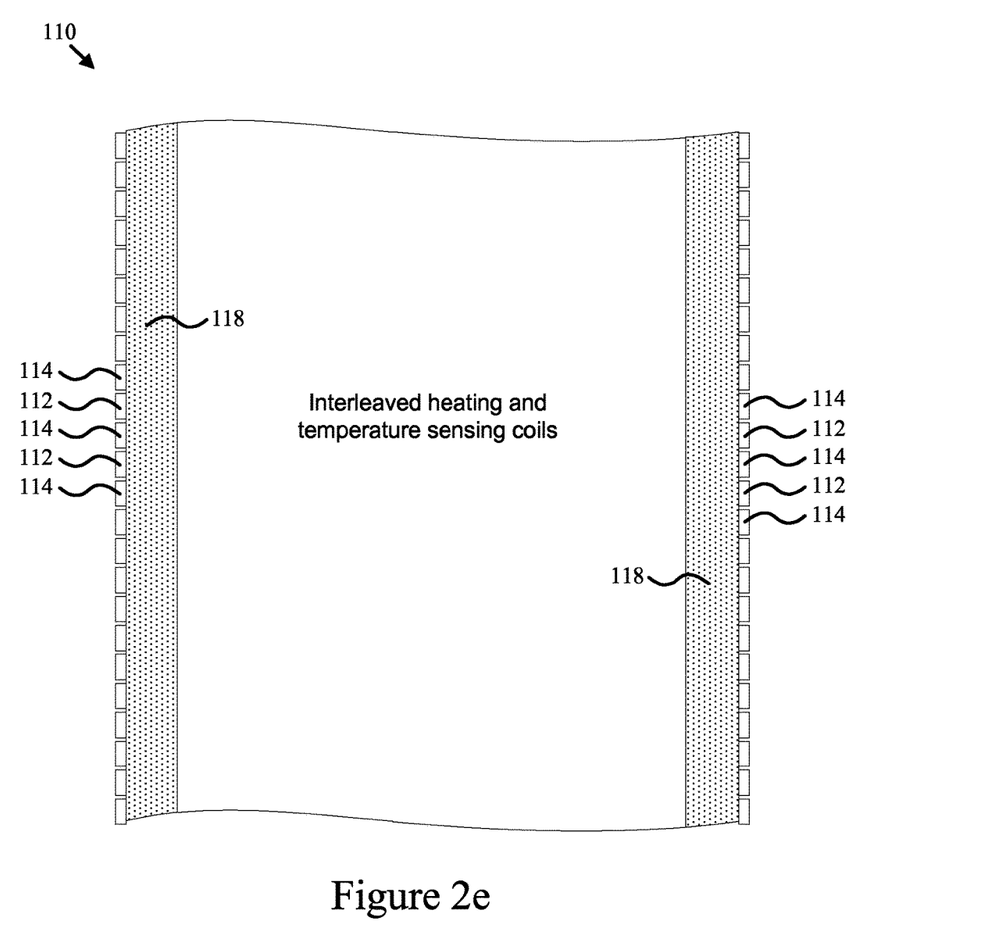

FIG. 2*e* depicts an embodiment of the reaction vessel 110 where the temperature sensing coils 112 and the heating coils 114 are interleaved. In the depicted embodiment, the coils 112 and 114 are wound onto, deposited on, or bonded to, the sample tube 118. In one embodiment, a conductive layer is deposited on the sample tube 118 and etched with a pattern to form the coils 112 and 114.

Figure 3:
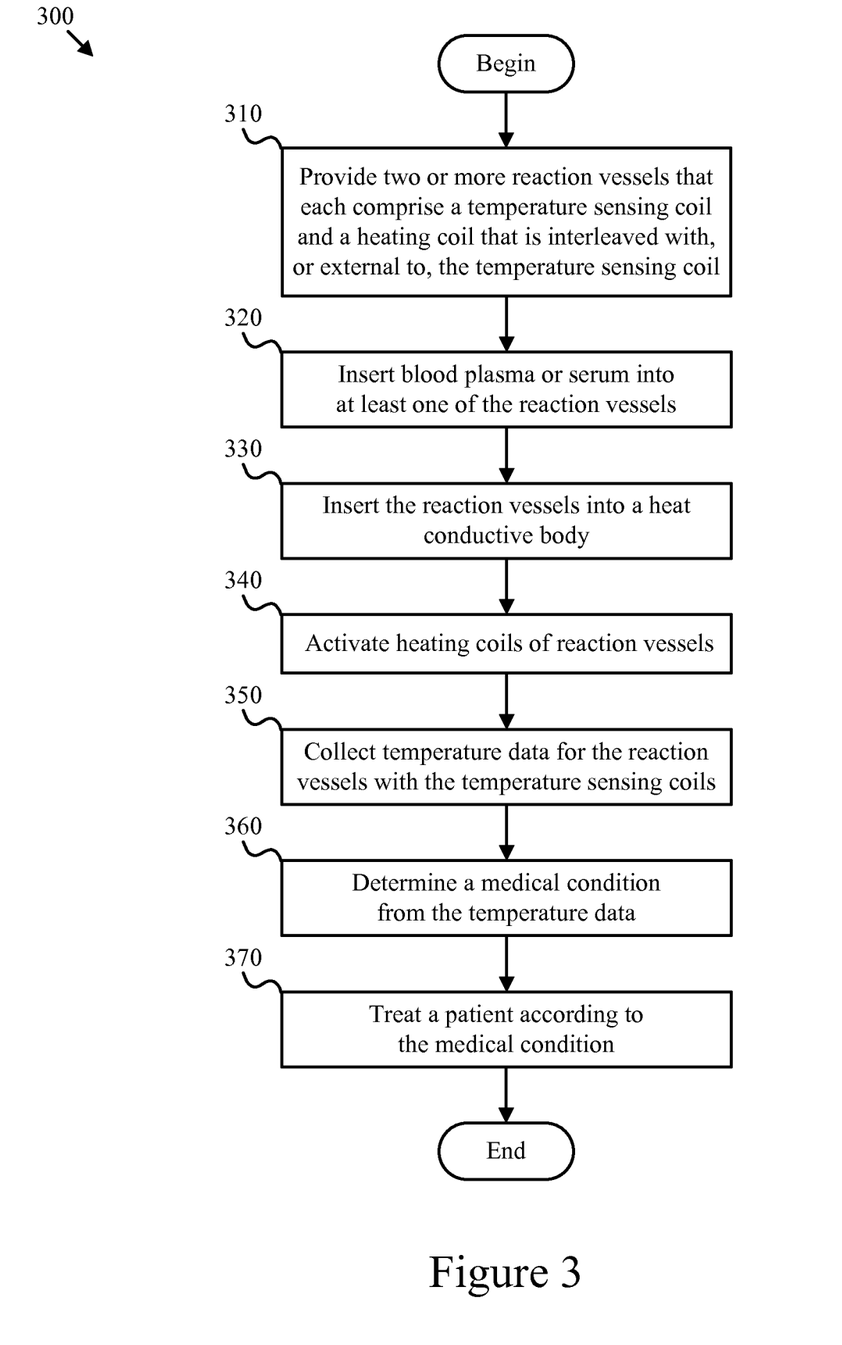
FIG. 3 is a flowchart depicting one embodiment of a thermogram measurement and utilization method.

FIG. 3 is a flowchart depicting one embodiment of a thermogram measurement and utilization method 300. As depicted, the method 300 includes providing 310 two or more reaction vessels, inserting 320 blood plasma or serum into one or more reaction vessels, inserting 330 the reaction vessels into a heat conductive body, activating 340 the heating coils of the reaction vessels, collecting 350 temperature data, determining 360 a medical condition, and treating 370 a patient according to the medical condition.

Providing 310 two or more reaction vessels may include providing reaction vessels that each comprise a temperature sensing coil, and a heating coil that is coaxial with and exterior to, or interleaved with, the temperature sensing coil.

Inserting 320 blood plasma or serum into one or more reaction vessels may include inserting the blood plasma or serum into non-reference reaction vessels. The blood plasma or serum may be mixed with a diluting liquid.

Inserting 330 the reaction vessels into a heat conductive body may include inserting each reaction vessel into a corresponding cavity within the heat conductive body that is shaped to conform to the profile of the reaction vessel.

Activating 340 the heating coils of the reaction vessels may include applying a voltage or current signal to the heating coils. In some embodiments, feedback from the temperature sensing coils is used to generate a specific temperature profile over time.

Collecting 350 temperature data may include recording data corresponding to the temperature sensing coils. The data may be differential calorimetric data that compares the temperature of, or heat emitted from, a reaction vessel containing blood plasma or serum with a reference reaction vessel.

Determining 360 a medical condition may include statistically matching the recorded data with data from samples corresponding to specific known medical conditions.

Treating 370 a patient according to the medical condition may include following a treatment regimen associated with the determined medical condition.

The apparatus and method presented herein provides a number of distinct advantages over prior art solutions. It should be noted that some of the functional units described herein, as well at the methods described herein, may be embodied as modules (not shown). For example, one or more modules may be configured to interface with, and generate thermograms from, the thermogram collection apparatus 100 according to the thermogram measurement and utilization method 300 or the like. The various modules may include a variety of hardware components that provide the described functionality including one or more processors such as CPUs or microcontrollers, or programmable logic devices (i.e., hardware components) that are configured by one or more software components. The software components may include executable instructions or codes and corresponding data that are stored in a non-transitory computer-readable storage medium such as a non-volatile memory, or the like. The instructions or codes may include machine codes that are configured to be executed directly by the processor. Alternatively, the instructions or codes may be configured to be executed by an interpreter, or the like, that translates the instructions or codes to machine codes that are executed by the processor.

It should also be understood that this description is not intended to limit the invention. On the contrary, the exemplary embodiments are intended to cover alternatives, modifications, and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. An apparatus for determining thermograms of blood plasma or serum, the apparatus comprising:
    two or more reaction vessels, each reaction vessel thereof comprising a temperature sensing coil, and a heating coil that is coaxial with and exterior to, or interleaved with, the temperature sensing coil; and
    a heat conductive body having two or more cavities formed therein for receiving the reaction vessels.

2. The apparatus of claim 1, wherein each heating coil comprises an electrically resistive material.

3. The apparatus of claim 2, wherein the electrically resistive material is selected from the group consisting of constantan and manganin.

4. The apparatus of claim 1, wherein each temperature sensing coil comprises a temperature sensitive material whose resistance is substantially sensitive to changes in temperature.

5. The apparatus of claim 4, wherein the temperature sensitive material is selected from the group consisting of nickel, copper, iron, platinum and various alloys.

6. The apparatus of claim 1, wherein each reaction vessel further comprises a sample tube that is coaxial with and interior to the temperature sensing coil.

7. The apparatus of claim 6, wherein the sample tube comprises glass or another unreactive material.

8. The apparatus of claim 1, wherein each reaction vessel further comprises a heat conductive tube that is coaxial with the temperature sensing coil and the heating coil.

9. The apparatus of claim 8, wherein the heat conductive tube is disposed interior to the temperature sensing coil and the heating coil.

10. The apparatus of claim 8, wherein the heat conductive tube is disposed between the temperature sensing coil and the heating coil.

11. The apparatus of claim 8, where the heat conductive tube comprises a first heat conductive material.

12. The apparatus of claim 11, wherein the first heat conductive material is selected from the group consisting of aluminum, copper, silver or gold.

13. The apparatus of claim 11, wherein the ea conductive body comprises a second heat conductive material.

14. The apparatus of claim 13, wherein the second heat conductive material is selected from the group consisting of aluminum, copper, silver or gold.

15. A method for determining thermograms of blood plasma or serum, the method comprising:
    providing two or more reaction vessels, each reaction vessel thereof comprising a temperature sensing coil, and a heating coil that is coaxial with and exterior to, or interleaved with, the temperature sensing coil; and
    inserting the reaction vessels into a heat conductive body comprising two or more cavities formed therein for receiving the reaction vessels;
    activating the heating coils of the reaction vessels; and
    collecting temperature data for the reaction vessels with the temperature sensing coils.

16. The method of claim 15, wherein each reaction vessel further comprises a heat conductive tube that is coaxial with the temperature sensing coil and the heating coil.

17. The method of claim 15, wherein each reaction vessel further comprises a sample tube that is coaxial with and interior to the temperature sensing coil.

18. The method of claim 15, further comprising generating a thermogram from the temperature data.

19. The method of claim 15, further comprising determining a medical condition from the temperature data.

20. The method of claim 19, further comprising treating the medical condition.

* * * * *